United States Patent

Py

[11] Patent Number: 5,366,499
[45] Date of Patent: * Nov. 22, 1994

[54] INTRAOCULAR PROSTHESIS

[75] Inventor: Daniel Py, Natick, Mass.

[73] Assignee: Keratos, Inc., Wellesley, Mass.

[*] Notice: The portion of the term of this patent subsequent to Apr. 5, 2011 has been disclaimed.

[21] Appl. No.: 178,946

[22] Filed: Jan. 5, 1994

Related U.S. Application Data

[63] Continuation of Ser. No. 978,645, Nov. 19, 1992, Pat. No. 5,300,115.

[51] Int. Cl.$^5$ .............................................. A61F 2/14
[52] U.S. Cl. ........................................ 623/4; 623/5; 623/6
[58] Field of Search .......................................... 623/4–6

[56] References Cited

U.S. PATENT DOCUMENTS

| | | | |
|---|---|---|---|
| 2,714,721 | 8/1955 | Stone | 623/5 |
| 2,754,520 | 7/1956 | Crawford, Jr. | |
| 3,454,966 | 7/1969 | Rosen | 623/4 |
| 4,043,331 | 8/1977 | Martin et al. | 128/156 |
| 4,044,404 | 8/1977 | Martin et al. | |
| 4,249,272 | 2/1981 | Poler | 623/6 |
| 4,253,199 | 3/1981 | Banko | |
| 4,285,073 | 8/1981 | Szycher | |
| 4,298,004 | 11/1981 | Schachar et al. | |
| 4,304,012 | 12/1981 | Richard | |
| 4,306,318 | 12/1981 | Mano et al. | |
| 4,323,525 | 4/1982 | Bornat | 264/24 |
| 4,345,414 | 8/1982 | Bornat et al. | 53/425 |
| 4,373,218 | 2/1983 | Schachar | |
| 4,409,691 | 10/1983 | Levy | |
| 4,470,159 | 9/1984 | Peyman | |
| 4,524,036 | 6/1985 | Gilding et al. | 264/10 |
| 4,550,713 | 11/1985 | Hyman | |
| 4,552,707 | 11/1985 | How | 264/24 |
| 4,586,929 | 5/1986 | Binder | 623/5 |
| 4,601,556 | 7/1986 | Siviglia | 351/160 R |
| 4,607,617 | 8/1986 | Choyce | |
| 4,612,012 | 9/1986 | White | 623/5 |
| 4,615,700 | 10/1986 | Federov et al. | 623/6 |
| 4,615,701 | 10/1986 | Woods | 623/6 |
| 4,615,702 | 10/1986 | Koziol et al. | 623/6 |
| 4,657,793 | 4/1987 | Fisher | 428/36 |
| 4,689,186 | 8/1987 | Bornat | 264/6 |
| 4,693,715 | 9/1987 | Abel | 623/5 |
| 4,715,858 | 12/1987 | Lindstrom | 623/5 |
| 4,798,607 | 1/1989 | Middleton et al. | 623/1 |
| 4,806,382 | 2/1989 | Goldberg et al. | 427/1 |
| 4,842,505 | 6/1989 | Annis et al. | 425/174.8 E |
| 4,842,599 | 6/1989 | Bronstein | 623/5 |
| 4,842,601 | 5/1989 | Smith | 623/6 |
| 4,865,601 | 9/1989 | Caldwell et al. | 623/5 |
| 4,883,453 | 11/1989 | Berry et al. | 600/36 |
| 4,932,968 | 6/1990 | Caldwell et al. | 623/6 |
| 4,965,110 | 10/1990 | Berry | 428/36.4 |
| 5,019,097 | 5/1991 | Knight et al. | 623/5 |

FOREIGN PATENT DOCUMENTS

| | | | |
|---|---|---|---|
| 333344 | 9/1989 | European Pat. Off. | |
| 2705234 | 8/1978 | Germany | 623/5 |
| 2120946 | 12/1983 | United Kingdom | |
| 1660694 | 7/1991 | U.S.S.R. | 623/5 |

Primary Examiner—Randall L. Green
Assistant Examiner—Mary Beth O. Jones
Attorney, Agent, or Firm—Kenyon & Kenyon

[57] ABSTRACT

A prosthesis for implanting in an eye has a lens member and a double interface member which is coupled to the periphery of the lens member. The double interface member is comprised of a more superficial branch and a deeper branch which project out from the lens member. The double interface member has a plurality of pores for permitting the ingrowth of tissue to anchor the prosthesis to the eye. The double interface member also has an anatomical structure into which eye tissue is inserted, so as to become an immediate anchor to the eye and an immediate barrier to external pathogens.

12 Claims, 3 Drawing Sheets

INTRAOCULAR PROSTHESIS

This application is a continuation of application Ser. No. 07/978,645 filed Nov. 19, 1992, now U.S. Pat. No. 5,300,115.

BACKGROUND OF THE INVENTION

1. Field of the Invention

The present invention relates to prostheses and, in particular, to ocular prostheses for replacing, for example, diseased or damaged corneas or portions of corneas.

2. Description of Related Art

Several attempts have been made to provide prostheses for the replacement of diseased or injured corneas. One such prosthesis is described in U.S. Pat. No. 4,865,601, which is intended to lie deep in an intra-lamellar stromal pocket and to be anchored in place by a fibrous ingrowth of tissue into an annular porous skirt of the prosthesis. The implant is anchored beneath the conjunctiva, which is sewn together in a flap over the eye, allowing for support for the six to eight weeks needed for the implant to root. The conjunctiva flaps open gradually between the sixth and eighth week during which time sight is gradually regained.

The prosthesis used in U.S. Pat. No. 4,865,601 includes an optical element made from polyurethane, which is surrounded by a porous annular skirt made from polytetrafluoroethylene ("Goretex"). The porous skirt is intended to permit the fibrous ingrowth of tissue. The optical element is bonded to the annular skirt by introducing a polymerization mixture into the area where the optical element and skirt overlap, to bond the two different materials together.

A problem in the art of prostheses for implantation in the eye involves breach of the barrier which protects the internal parts of the eye, thereby allowing for invasion by external pathogens and resultant infections. Previous attempts to alleviate this problem have used prostheses, or parts thereof, made of a porous material into which eye tissue can grow to create a barrier. Such a barrier, however, is dependent on sufficient ingrowth of tissue into the porous material and can take from weeks to months to develop.

Protective measures, such as the surgical creation of the conjunctival flap discussed above, must be taken during the corneal fibroblast ingrowth in the pores for two main reasons: (1) to protect the eye from external pathogens during this period, and (2) to prevent the epithelial downgrowth of the conjunctival cells in-between the wound edges, by directing them on top of the inert synthetic material of the prosthesis where they have no chance to be anchored and, therefore, no chance of reaching the wound before the healing process performed by the ingrowth of the corneal fibroblast in the pores of the peripheral prosthesis occurs. In the case of conjunctival flaps, the patient does not regain vision until at least six to eight weeks after surgery.

Another related problem with the background art relating to ocular protheses is that specific surgical procedures, such as the creation and sewing together of the conjunctival flaps, must be performed after a broad dissection of the conjunctiva which will not feed into the inert material of the prosthesis.

Accordingly, it is an object of the present invention to provide a corneal implant which enables the patient to see immediately after surgery.

Another object is to provide an ocular prosthesis which permits the use of eye tissue, such as the conjunctiva, as a means of immediately anchoring the prosthesis to the eye during surgery.

Another object is to provide an ocular prosthesis wherein eye tissue, such as conjunctiva tissue, may be actively directed to an anatomical synthetic for its insertion in a way to prevent epithelial down growth and to create an anatomical and clearly limited barrier against any external pathogens.

A further object is to provide a simpler surgical procedure for implanting an artificial cornea, resembling that which is used for corneal transplants.

SUMMARY OF THE INVENTION

The present invention is a prosthesis for implanting in the eye, comprising a lens member and a double interface member. The lens member can be made from almost any optically clear, bio-compatible polymer. The double interface member, which is composed of a porous woven or non-woven fabric or material, has two layers or branches: a deeper layer which is inserted within the corneal stroma in its extreme periphery and a second, more superficial layer which is inserted between the conjunctiva and the most superficial layer of the very peripheral cornea. The double interface member is coupled to the periphery of the lens member in an annular groove defined in the periphery of the lens. The double interface member contains a multiplicity of pores for permitting the ingrowth of tissue to serve as a secondary anchor and barrier, and which is adapted to receive the purse string suture of the conjunctiva.

Therefore, the double interface member also has an anatomical structure into which the conjunctiva is actively directed. Thus, the prosthesis is immediately anchored to the eye and an anatomical and clearly limited barrier is immediately formed to prevent external pathogens from contaminating the intraocular fluids and the above mentioned epithelial downgrowth. In one embodiment of the invention, this anatomical structure is a superficial peripheral annular groove, which is in continuity with the more superficial layer of the double interface member. The eye tissue contemplated in this embodiment is conjunctiva tissue, which is forced into the groove of the double interface member by use of a purse string suture. The groove is covered with the porous material of the double interface member This allows the conjunctiva to grow into the interface, thereby creating a new anatomical limit of the conjunctiva which acts as a secondary anchor and barrier for the prosthesis.

One advantage of the prosthesis of the invention, is the immediate, strong connection made between the prosthesis and the eye, which is accomplished in a number of different ways. First, the invention anchors the prosthesis at two different levels in the eye: at the level of the deeper layer in the stroma and at the level of the more superficial layer between the conjunctiva and the most superficial layer of the very peripheral cornea. Second, eye tissue is forced into the anatomical structure of the double interface member and then attached to the superficial branch or layer thereof, serving as an immediate anchor to the eye. This anchor is strong enough to eliminate the need for additional support, such as a conjunctival flap, during the time that the implant is rooting. Thus, the rooting serves only as a secondary means of anchor, rather than as the primary means that it assumes in the background art.

Another advantage of the prosthesis of the present invention is that sight is possible immediately after implant of the prosthesis. This is possible because the conjunctival flap provides tight protection from external pathogens when it is sutured with a purse string suture within the annular groove.

In addition, the inventive ocular prosthesis is more resistant to trauma and allows surgeons to use a routine surgical procedure similar to that already used in corneal transplants. This is a distinct improvement over methods such as that used with U.S. Pat. No. 4,865,601, discussed above, which requires surgeons to learn a surgical procedure specific to that particular device.

Other advantages and features of the prosthesis of the present invention will become apparent in view of the following detailed description and accompanying drawings.

DETAILED DESCRIPTION

Figure 1:
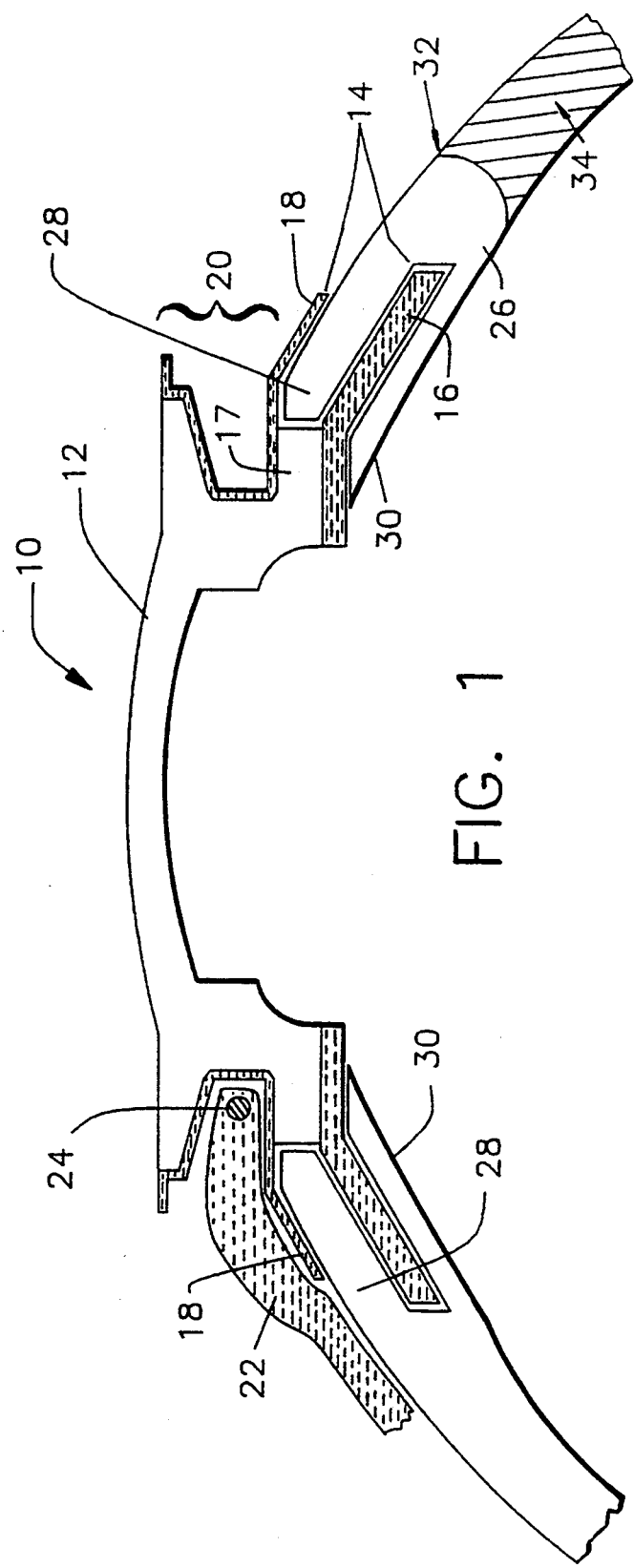
FIG. 1 is a cross-sectional view of a prosthesis in accordance with the present invention as implanted in the eye.
Figure 2:
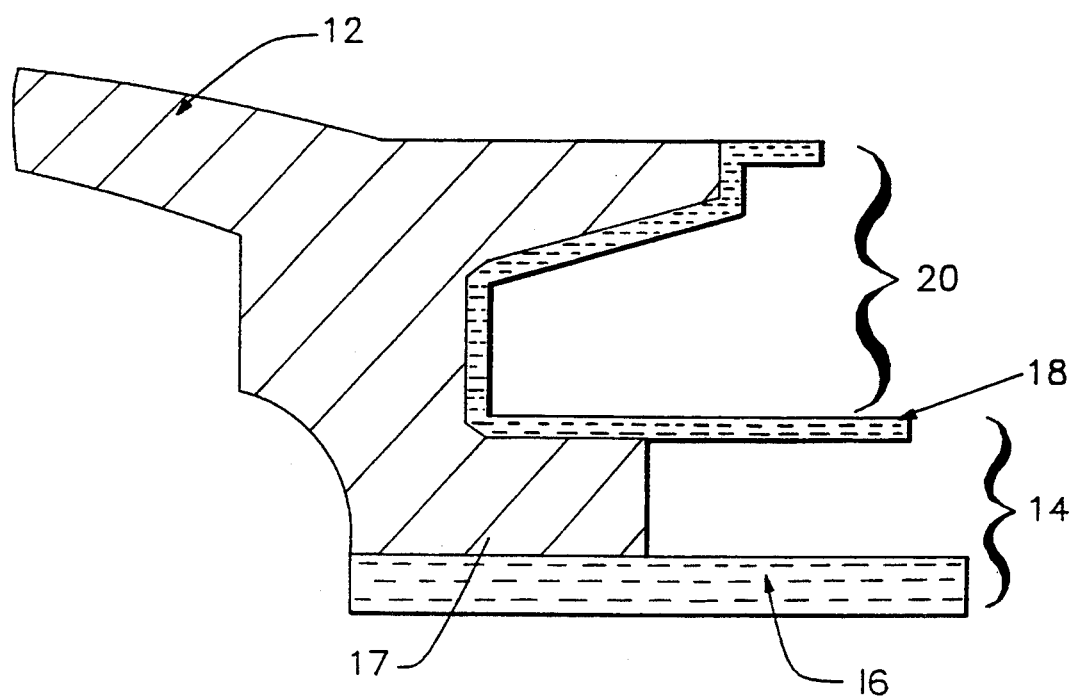
FIG. 2 is a partial, cross-sectional view of a prosthesis in accordance with the invention, focusing on the periphery where the porous interface is insert molded in the optic.

In FIG. 1, a prosthesis in accordance with the present invention is indicated generally by the reference numeral 10. The prosthesis 10 includes a lens member or optic 12 which is coupled around its periphery to a double interface member 14. The double interface member 14 includes a deeper branch or layer 16 and a more superficial branch or layer 18 which project in a radially outward direction from the periphery, and the member 14 has an anatomical structure or recess into which eye tissue is directed.

Figure 3:
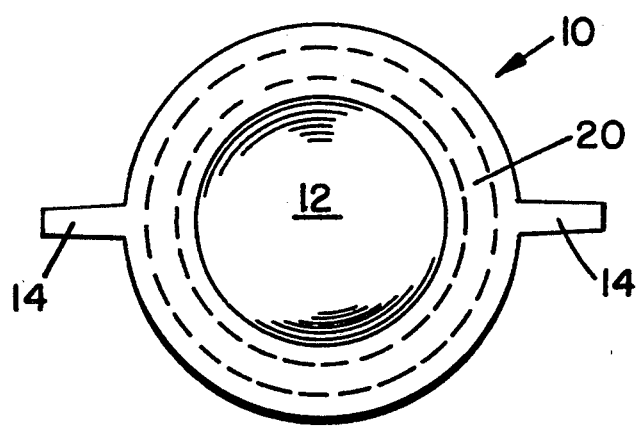
FIG. 3 is a top, elevational view of the prosthesis illustrated in FIG. 1.

The double interface member 14 is attached (for example, by an insert molding technique) around the periphery of optic 12. The double interface member 14 may be a single continuous member attached around the periphery of optic 12, or it may consist of a plurality of separate and discrete individual double interface members attached around the periphery of optic 12 at spaced intervals. For example, the prosthesis 10 may include two separate double interface members 14, spaced apart on opposite sides of the periphery of the lens member. (See FIG. 3)

In the preferred embodiment, the anatomical structure is a superficial peripheral circular groove 20 which may be continuous with the more superficial branch 18 of the double interface member 14. The superficial branch 18 and the deep branch 16 define a gap therebetween for receiving at least the superficial layer 28 of the corneal stroma. The superficial branch 18 may be separated from the deep branch 16 by an outward projection 17 of the optic 12.

As illustrated, the periphery of the optic 12 is also configured to define a peripheral groove for receiving the groove 20 of the superficial branch 18. In this way, the groove 20 lines the corresponding groove in the periphery of the optic 12. The eye tissue which is directed into the groove 20 is conjunctiva tissue 22, which my be forced into the groove using a purse string suture 24.

As is described below, the prosthesis 10 of the present invention may be used to replace a diseased or damaged portion of a cornea which has been surgically removed. Briefly, the prosthesis 10 is implanted in an eye by first surgically extracting the whole thickness of an approximately 7 mm diameter central cornea. The remaining peripheral portion of the cornea is dissected in the middle of the corneal stroma 26 to result in a superficial layer 28 and a deep layer 30. The deeper branch 16 of each of the double interface members 14 is inserted into the corneal stroma 26 between layers 28 and 30 up to the extreme periphery of the corneal stroma, the limbus 32, as illustrated in FIG. 1. The deeper branch may be sutured to the side of the limbus 32 and to the sclera 34. Next, the more superficial branch 18 of the annular double interface member 14 is inserted between the conjunctiva 22 and the most superficial layer of the very peripheral cornea. Finally, the conjunctiva eye tissue 22 is forced into each annular groove 20, thereby immediately anchoring the prosthesis to the eye.

The layers 16 and 18 of each double interface member preferably have a constant thickness throughout. Preferably, the deeper layer 16 projects approximately 2.75 mm out from its point of attachment to the lens periphery and the more superficial layer 18 projects approximately 1.50 mm out from its point of attachment to the lens periphery. The diameter of the lens member 12 is approximately 6.50 mm. Preferably, the radial distance from the center of the lens 12 to the free end of the deeper branch 16 is approximately 5.75 mm and the radial distance from the center of the lens 12 to the free end of the more superficial branch 18 is approximately 5 mm. Preferably, the deeper branch is approximately 0.25 mm thick and the more superficial branch is approximately 0.20 mm thick. Preferably, the lens member 12 is approximately 0.5 mm thick in its central area, and is defined by the posterior radius of curvature which is approximately 7.5 mm. These dimensions are purely exemplary, however, and can be changed as required depending upon the needs of each particular patient.

The specific curvature and thickness of the lens member 12 can also vary depending upon each particular patient's optical requirements in a manner known to those skilled in the art. However, due to the significant cost of the manufacturing tools, the prosthesis is preferably manufactured with the same radius of curvature, leaving to the operator, the optical adjustment to be made with the intraocular lens which typically replaces the crystalline lens in cataracted or blind patients. The intraocular lens is put in the interior or the posterior chamber. The determination of the intraocular lens is based on an average 44 diopters value for the artificial cornea.

The lens member 12 can be made of any optically clear bio-compatible polymer known in the art, such as an aliphatic, polyether-based polyurethane. The double interface member 14 can be made of almost any porous woven or non-woven bio-compatible fabric or material known in the art. In the preferred embodiment, the double interface member 14 is also made of an aliphatic, polyether-based polyurethane, and the material is spun electrostatically to form pores (not shown). Other suitable materials are described in U.S. Pat. No. 4,865,601, such as polytetrafluoroethylene, polyester and collagen.

The technique for electrostatically spinning polyurethane to form porous polyurethane is known to those skilled in the art and explained, for example, in U.S. Pat. Nos. 4,043,331, 4,044,404, and 4,552,707. A liquid solution of the polyurethane, extruded into fibers, is introduced into an electric field, wherein the liquid is caused to produce fibers. The solution is made by dissolving the polyurethane into a suitable solvent, such as DMAC, in a manner known to those skilled in the art. The solution is discharged through an array of nozzles into the electric field, which is generated between a rotating mandrel charged with a potential of approximately 12 KV, and ground. As the solution is discharged from the array of nozzles toward the charged mandrel, the solution (DMAC) evaporates and, as a result, polyurethane fibers approximately 1 micron in diameter are laid down on the mandrel. The array of nozzles is continuously moved over the mandrel, thus forming a layer of micro-porous polyurethane. The pore size can be controlled in a manner known to those skilled in the art, and preferably the pore dimensions should be maintained within the range of approximately 50 to 600 microns. In the embodiment of the present invention illustrated, the average pore dimension is preferably on the order of approximately 200 microns.

The electrostatically spun, porous polyurethane is preferably formed in sheets equal in thickness to the desired thickness of the deep layer 16 of the double interface member 14. Thus, in the embodiment of the prosthesis 10 illustrated, the porous polyurethane sheets would be approximately 0.25 mm thick. The material used, for the superficial layer 18 can be the same porous polyurethane used for the deeper layer 16 or, as currently used a polyester-woven single layer with a 300 micron pore size available from SAATI Company of Stamford, Conn.

The lens member 12 and double interface members 14 can be made of the same material as described in my copending application Ser. No. 07/702,048. One possible material for both the lens and the double interface members is the aliphatic, polyether-based polyurethanes, such as the Tecoflex medical grade polyurethane resins, available from Thermedics, Inc. of Woburn Mass. Tecoflex grade EG80A is particularly satisfactory. One advantage of using an aliphatic, polyether-based polyurethane, is that it is biocompatible, inert, non-biodegradable and UV stable, thus providing an inherently safe prosthesis which substantially avoids the degradation and biocompatibility problems encountered in the use of prior prosthesis.

The lens 12 is preferably injection molded in a manner known to those skilled in the art to obtain the best optical resolution and consistent quality. Because the polyether-based polyurethane is a relatively viscous material, the runners leading to the mold cavity of the injection molding apparatus are preferably heated to maintain the polyurethane at a higher temperature and, thus, a lower viscosity upon injection into the mold cavity. Also, additional cavities for receiving the polyurethane, typically referred to as "cold shots", are coupled to the runners immediately prior to the gate where the polyurethane is injected into the mold cavity. The cold shots are provided to receive the polyurethane located closer to the walls of the runners which might tend to granularize. As a result, only the hottest polyurethane (and most homogeneous) it injected through the gate into the mold cavity, whereas the polyurethane that might tend to granularize flows off into the cold shots. Also, the surfaces of the die cavity are preferably chilled in order to prevent the formation of flow lines on the surfaces of the lens member 12, and to prevent warpage of the lens member 12 upon removal from the mold, and to obtain the best optical resolution and consistent quality.

The prosthesis of the invention may be formed to firmly secure the porous double interface member to the lens using, for example, the method which is the subject of my copending U.S. application Ser. No. 07/818,074 filed on Jan. 8, 1992, entitled Molded Article and Method and Apparatus for Molding the Article. In accordance with this method, before the lens is molded, two discs of porous material for the porous double interface member are inserted into the mold by compressing them between dies of the mold.

When the prosthesis 10 is used for replacing a diseased or damaged portion of a cornea, it may typically be referred to as a keratoprosthesis by those skilled in the art. It should be pointed out, however, that the features of the present invention are equally applicable for numerous other types of prosthesis.

What is claimed is:

1. A prosthesis suitable for implantation in an eye, comprising:
    a lens having a peripheral edge, the peripheral edge being configured with a groove therein; and
    a plurality of eye interface members coupled to the lens along the peripheral edge, each interface member having a portion which is configured in a shape which corresponds to said groove and which lines at least an arc of the groove along the peripheral edge for receiving conjunctiva eye tissue, and each interface member having an upper layer and a lower layer which project outwardly from the lens peripheral edge, the upper layer and the lower layer defining a gap therebetween for receiving corneal stroma tissue of an eye.

2. The prosthesis according to claim 1, wherein the lens has a diameter which is equal to that of a human cornea diameter.

3. The prosthesis according to claim 1, wherein each eye interface member has defined therein a plurality of pores for permitting ingrowth of eye tissue.

4. The prosthesis according to claim 3, wherein the pore size is from 80 to 500 microns in diameter.

5. The prosthesis according to claim 1, wherein the upper layer of each eye interface member is a continuous extension of the portion of the eye interface member which lines the groove of the peripheral edge of the lens.

6. The prosthesis according to claim 1, wherein the upper layer is separated from the lower layer of each eye interface member by a projection of the lens.

7. The prosthesis according to claim 5, wherein the upper layer is separated from the lower layer of each eye interface member by a projection of the lens.

8. The prosthesis according to claim 1, wherein the lens is made from an optically clear bio-compatible polymer and each interface member is made from a porous woven or non-woven material.

9. A method for replacement of a cornea of an eye with the ocular prosthesis according to claim 1, comprising the steps of:
    surgically removing a central section of the cornea to leave at least a peripheral portion of the corneal stroma in the eye,
    dissecting a peripheral portion of the corneal stroma into an upper layer and a lower layer,
    inserting and attaching the lower layer of each eye interface member between the corneal stroma layers, inserting and attaching the upper layer of each eye interface member between the conjunctiva and the upper corneal stroma layer, and inserting and attaching conjunctiva eye tissue into the groove portion of each eye interface member to anchor the prosthesis to the eye.

10. The method according to claim 8, wherein the conjunctiva eye tissue is attached to the groove using a purse string suture.

11. The method according to claim 9, wherein each eye interface member has defined therein a plurality of pores for permitting ingrowth of eye tissue and anchoring the prosthesis to the eye.

12. The method according to claim 9, wherein the lower layer of each eye interface member is attached by suturing it to the scleral side of the limbus of the corneal stroma.

* * * * *